United States Patent [19]

Alers et al.

[11] 4,048,847
[45] Sept. 20, 1977

[54] NONDESTRUCTIVE DETECTION OF STRESS

[75] Inventors: George A. Alers; Robert B. Thompson, both of Thousand Oaks, Calif.

[73] Assignee: Rockwell International Corporation, El Segundo, Calif.

[21] Appl. No.: 705,213

[22] Filed: July 14, 1976

[51] Int. Cl.$^2$ ............................................ G01N 29/00
[52] U.S. Cl. .......................... 73/67.5 R; 73/71.5 US; 73/88.5 R
[58] Field of Search ............ 73/67.5 R, 67.6, DIG. 2, 73/DIG. 4, 71.5 US, 88.5 R, 67.1

[56] References Cited

U.S. PATENT DOCUMENTS

| 2,461,543 | 2/1949 | Gunn | 73/67.5 R X |
| 3,555,887 | 1/1971 | Wood | 73/67.5 R |
| 3,861,206 | 1/1975 | Kawafune et al. | 73/141 R |

*Primary Examiner*—James J. Gill
*Attorney, Agent, or Firm*—L. Lee Humphries; Craig O. Malin

[57] ABSTRACT

Stress is detected by magnetostrictively generating vibrations which are detected at a location spaced from the region of generation. The efficiency of the generation is indicative of stress if the region is magnetically biased to less than maximum amplitude for the vibrations as produced. Preferably, the needed bias for generating vibrations at a constant level is used as stress indicator. Due to reciprocity of magnetostriction, the efficiency of generating magnetic oscillations by means of elastic vibrations in a biased region can be detected.

30 Claims, 6 Drawing Figures

NONDESTRUCTIVE DETECTION OF STRESS

The invention herein described was made in the course of or under a contract or subcontract thereunder, [or grant] with the United States Air Force.

BACKGROUND OF THE INVENTION

The present invention relates to the detection of stress conditions and other internal properties in structural materials, such as plastic deformation, dislocations, and other microstructure features.

The following presentation presents a brief summary of certain aspects of the state of the art, pertaining to different fields which, more often than not, have remained unrelated to each other.

Nondestructive inspection of structural materials has been used in the past and gains increasingly in importance. One uses a variety of different phenomena such as x-raying the part of probing it with ultrasonic energy. In regards to the latter, a variety of techniques have been developed including the development of transducers which launch ultrasonic waves into the structural material so that the waves may interact therewith. That interaction, for example a reflection by a flaw, fault, etc., will be detected, e.g., upon return of the wave.

One kind of these transducers is, for example, constructed in that it generates itself the ultrasonic waves which are then transmitted to and into the part under investigation. Another kind of transducer (see e.g. U.S. Pat. No. 3,850,028) is of the electromagnetic variety in that h.f. electrical energy is coupled to the part and converted therein into elastic vibrations, on the basis of the Lorentz force. Other transducers are known which use magnetostriction to convert an oscillatory magnetic field into elastic vibrations. Thus, such a transducer generates the vibration in the structural material, and the vibration propagate from the point or region of generation further into the part for interaction as described.

Aside from the foregoing, investigations by various physicists have discovered that the magnetostrictive property of steel depends on stress. See, for example, Bozorth, Ferromagnetism (D. Van Nostrand Co. Inc., Princeton) 1951, p. 656; Allen, Haborak, and Kao, "The Effect of Stress on the Magnetostriction of Iron, Nickel, and 49 Permalloy", Report THEMISUND-70-9 (Notre Dame, 1970) AD-711094; and Kuruzar and Cullity, Intern. J. Magnetism 1 (1971), pages 323–325.

DESCRIPTION OF THE INVENTION

It is an object of the present invention to provide a new and improved method for detecting local stress conditions in structural materials, and other internal properties.

In accordance with the preferred embodiment of the present invention, it is suggested to measure, e.g. local stress conditions, plastic deformations, dislocations, etc., in a structural material exhibiting magnetostriction, either by generating vibrations in a limited region of the material through interaction thereof with a variable magnetic field, or by causing vibrations to generate a variable magnetic field, and by determining the efficiency of this generating process, for example, through detection of the amplitude of an ultrasonic wave which resulted from the generation of the vibrations and at a point spaced-apart from the region that participated in the primary generative process, or through detection of the variable magnetic field, produced by arriving elastic vibrations.

Generally speaking, magnetostrictive oscillations are generated in a magnetically biased region, and the efficiency of the generation is detected as an indication of the microstructure features such as stress, plastic deformation, etc. The magnetostrictive oscillations are either elastic vibrations generated by a variable magnetic field, or a variable magnetic field results from elastic vibrations arriving at the biased region.

Stress determination can be had either by comparing, for example, with each other the efficiencies of the generation of magnetostrictive oscillations at different locations of the same part, or by generating separately a standard indication using a different part but of the same material and having known stress conditions (e.g. being stress free), and by comparing again the resulting efficiencies with each other.

The generation of vibrations by means of magnetostriction is the result of magnetically biasing the material to a particular magnetostrictive state and of superimposing an oscillatory component which is directly responsible for the generation of vibrations at the frequency of the magnetic field variations. The invention is based on the discovery that the efficiency of that generation depends on the magnetic bias in that the characteristic of efficiency vs. bias exhibits a rather complex, fine structure. That fine structure was found to be dependent to a considerable degree on the stress conditions of the region in the structural material which participates in the generation of the elastic vibrations. The efficiency of the generation is determined on the basis of the vibration amplitude as detected by a suitable pickup transducer in relation to the particular magnetic bias (being the zero point for the superimposed oscillatory component). This efficiency yields directly information on the stress conditions of the region in which the vibrations originate. For example, compression stress tends to render the complexity of the fine structure more pronounced in iron, while tensile stress tends to obliterate the complexity.

Broadly speaking the efficiency of the generation is the relationship between detected amplitude of an emitted wave and the external conditions for generating the vibrations. The efficiency of generating elastic vibrations can be defined in that for (i) a particular magnetic bias (ii) a particular amplitude of a variable magnetic field will produce an elastic vibration which is detectible beyond the region of vibration at (iii) a particular amplitude. Two of these three variables can be maintained constant, and the variation of the third variable is available as a representation of the stress in the region of generation of the elastic vibrations. Particular conditions, materials and objectives may render one of these possibilities more desirable, reliable or otherwise preferable over the respective other two. The efficiency is detectible in that a detected vibration will vary its amplitude if the stress conditions are changed, or if a different region with different stress conditions is used to generate vibrations, leaving the conditions of the generation the same. Alternatively, efficiency is detectible as a stress indication in that the conditions of generating vibrations are varied to obtain the same output of detection. Specifically, the generative conditions have as principle parameter the magnetic bias. For a constant magnetic bias, the detected amplitude of the emitted vibrations varies with stress; for a constant detected vibration amplitude the bias must be adjusted for different stress conditions. The latter mode of deriving a representation of efficiency was found to be preferred. For best results in iron or low carbon steels, the magnetic bias or range of bias should be limited to magnetic field strength below the value for maximum efficiency of vibration production because it was found that the maximum remains relatively invariant to stress.

The third free variable in this system is the amplitude of the variable magnetic field component. However, the complexity of the fine structure of the received amplitude vs. magnetic bias field and its variation with stress, renders the variations in that amplitude (to obtain a constant level of the detected signal) less reliable as an indicator, because of possible ambiguities. However, for fine structure and detail studies of minor load/stress variations, one may well vary the amplitude of the oscillating magnetic field and keep the bias constant for detecting a constant vibration level. In that case, the range of variations will be limited so that a likelihood of ambiguities is reduced.

The process above can be inverted in that elastic waves are launched in some fashion other than through employment of magnetostriction in the in situ generation. The waves are electromagnetically picked up in a region being magnetically biased and the magnetic field variations generated in that biased region on account of the elastic vibrations are picked up. The efficiency of that generation process vis-a-vis the launching is also an indicator of stress conditions for a particular bias, In effect, the inventive method works in either direction of magnetostriction due to the reciprocity of cause and effect between magnetic field oscillations on the one hand, and elastic vibrations on the other hand. The generation process in either case is dependent upon stress conditions, plastic deformations, etc., provided a suitable magnetic bias affects the region under investigation.

DESCRIPTION OF THE DRAWINGS

While the specification concludes with claims particularly pointing out and distinctly claiming the subject matter which is regarded as the invention, it is believed that the invention, the objects and features of the invention and further objects, features and advantages thereof will be better understood from the following description taken in connection with the accompanying drawings in which:

Proceeding now to the detailed description of the drawings, FIG. 1 shows a piece of structural material 1, such as ferromagnetic metal, e.g. steel. It is assumed that the region shown is subjected to a particular magnetic field $H_o$ setting up a magnetization $M_o$ in the material. A conductor 2 is laid across the surface of part 1 and is assumed to be flown through by an electric current $I_\omega$ of alternating magnitude. As a consequence, a magnetic field $H_\omega$ of alternating direction surrounds the conductor 2 and induces in the material 1 eddy currents $J_\omega$ and an alternating magnetization $M_\omega$ which is added (vector addition) to the bias magnetization $M_0$.

As a consequence of the foregoing, two different phenomena are observed with the same result as observable externally. In the case of a relatively large bias, e.g. in the order of kilooersteds, the oscillating eddy current developed in the material and interacting with the magnetic bias field produce a Lorentz force of a magnitude sufficient to generate mechanical oscillations in the material. For high frequencies and/or large material thickness, mechanical surface waves are set up. For lower frequencies and/or smaller material thickness, the oscillations are primarily Lamb waves.

For smaller values of the magnetic bias, say, a few hundred oersteds and less, the Lorentz forces are relatively insignificant, but magnetostriction is effective in that the oscillating component produces corresponding mechanical oscillations, whereby again a high frequency will predominantly produce surface waves.

Figure 2:
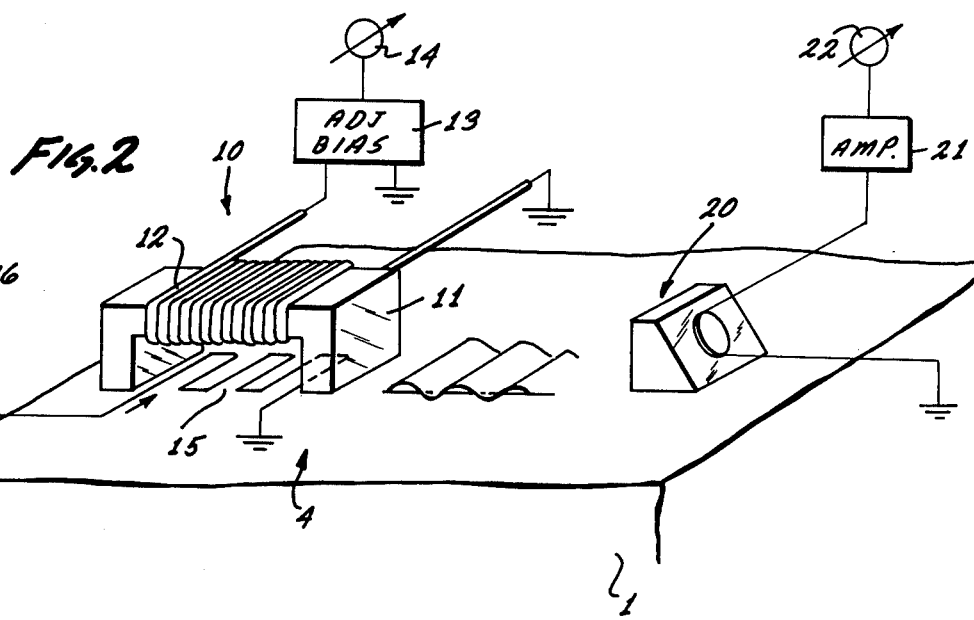
FIG. 2 is a perspective view, showing somewhat schematically equipment, including vibration generating transducer and pickup transducer and associated circuitry, for practicing the inventive method.

In order to generate efficiently such surface waves, on one hand, and to detect the surface waves as so produced, on the other hand, an arrangement can be used as shown in FIG. 2. Again, reference numeral 1 refers to a piece of structural material and a transmitter 10 is disposed on the surface as shown in the left hand portion of the drawing. The transmitter can be of the variety disclosed in U.S. Pat. No. 3,850,028. For purposes of the invention, only the essential components of such a surface wave launching transducer need to be shown and discussed.

A soft magnetic core 11 has two legs respectively ending in flat poles which are positioned to be in close proximity to the surface of part 1. The core 11 carries a coil 12 for inducing a static magnetic field. The field lines run from one pole to the other through a portion 4 of the subsurface region of part 1. The block 13 denotes schematically the source for energizing current durrent flowing through coil 12. It is presumed that the current is adjustable, for example, by adjusting the voltage applied to the coil. Instrument 14 indicates the d.c. current or the d.c. voltage applied to the coil 12 as a measured quantity being indicative of the magnetization bias produced in the region 4.

The transducer 10 includes additionally a flat coil 15 being actually a meandering conductor. The conductor may be a plating on a small PC board. This coil 15 is disposed between the legs of the core 11, directly above the premagnetized region 4 of structural part 1.

A source 16 of h.f. signals having frequency of, e.g., 160 KHz, is electrically connected to the coil 15. It is a primary characteristic of this coil 15 that it consists of a plurality of parallely positioned conductors being interconnected so that adjacent conductors are passed through by current in opposite directions. Moreover, the spacing between the conductors is equal to half a wavelength of any mechanical oscillation set up in the part 1 on account of the alternation in current flow through the conductors of the coil. Of course, the conductors of coil 15 extend transversely to the direction of bias by the magnet 11.

Figure 1:
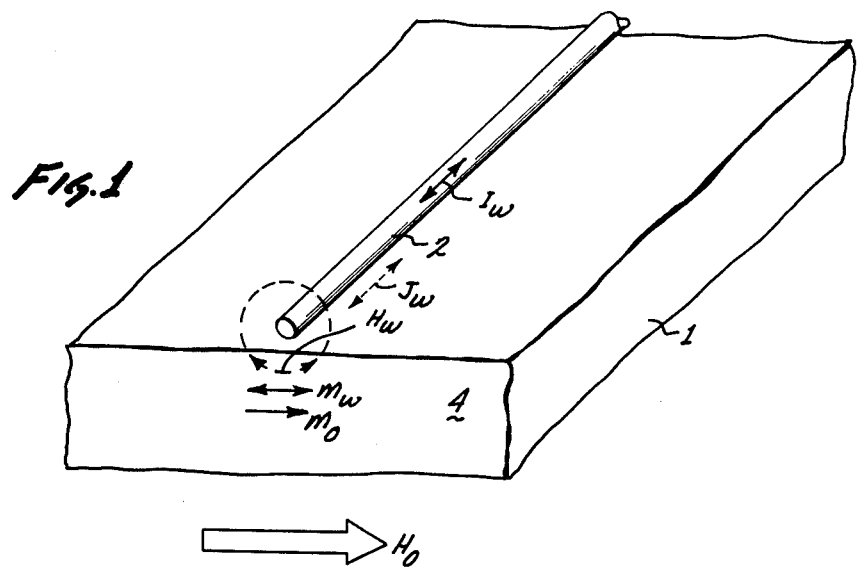
FIG. 1 is a perspective view of a part of structural material showing magnetic fields and current contributing to the electromagnetic generation of vibrations.

The system thus produces the magnetic phenomena as shown in and explained with reference to FIG. 1. More specifically, the current as flowing through coil 12 biases the region 4 magnetically in a particular direction. As an alternating current flows through coil 15, the region 4 is subjected to a spatial pattern of changes in the magnetostrictive length changes; the pattern corresponds to the wavelength of vibrations having frequency equal to the frequency of the oscillating current in coil 15. Thus, surface waves are launched to propagate away from transducer 10 primarily in the directions transversely to the extension of the long individual conductor elements of the coil 15. The efficiency of the generation of these vibrations depends on the particular bias as applied to region 4 as will be explained shortly.

A pickup transducer 20 such as a piezoelectric wedge or any other suitable transducer, is disposed on the surface of part 1 and at a distance of a few inches from the transducer 10 but in the direction of propagation of surface waves launched by transducer 10. The spacing between transducers 10 and 20 is such that feedthrough, i.e., electromagnetic coupling between them, is avoided. On the other hand, the gain of the system is enhanced if one places the transducers as close to each other as possible. Moreover, the detection and measurement is undertaken here for purposes of detecting the generation of vibrations, and the propagation should influence the amplitude of the detected waves as little as possible, preferably not at all. Since the transducers can be shielded from each other, a spacing of a few centimeters, or a few inches, was found suitable and adequate.

The transducer 20 is of conventional construction and develops an electrical signal upon receiving surface waves. That signal is amplified in a stage 21 and indicated by an instrument 22. Since only the amplitude of the detected wave is of immediate interest, state 21 may include a rectifier and filters so that the signal fed to the instrument 22 is d.c.

Figure 3A:
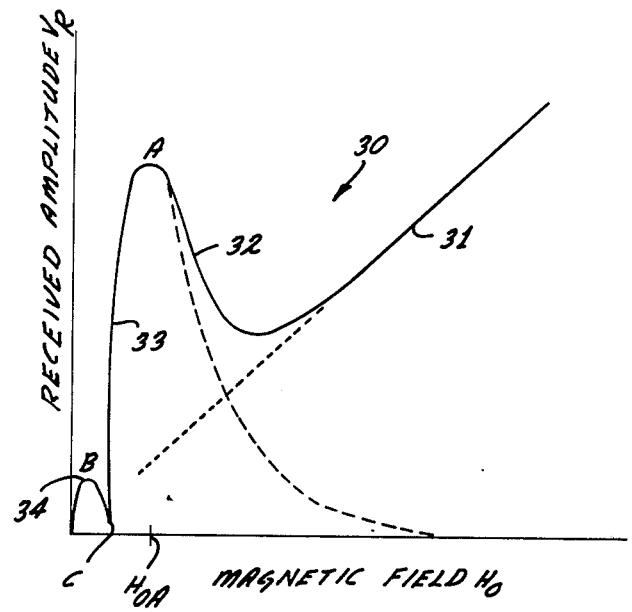
FIG. 3a is a graph showing signal amplitude as received by the pickup transducer plotted against magnetic bias produced by the generating transducer in the equipment shown in FIG. 2.

FIG. 3a is a plot showing the amplitude $V_r$ of a surface wave received by transducer 10 for a constant amplitude of energizing h.f. signals from source 16, but with variable bias as per adjustment of source 13. Thus, the curve 30 represents the efficiency of the generation of vibrations as it varies with the bias point. The amplitude of the oscillating magnetic field $H_\omega$, as superimposed upon the bias, is small in relation to the strength of the biasing field $H_o$. The curve as such is actually a somewhat schematic representation of the efficiency of generation of vibrations, and the contour of various portions may differ with the specific composition of the material. However, this basic contour is deemed valid for low carbon steel and iron. Other substances exhibiting magnetostriction have efficiency curves of different fine structure but in most instances, there is a pronounced peak A.

Illustrated curve 30 has a variety of branches of which the branch 31 is valid for higher (kilo-oersted) magnetic biasing fields, showing straight proportionality between surface wave amplitude as received and magnetic bias. The oscillations produced are the result of the Lorentz force, and the curve has qualitative validity for all metals in which eddy currents interact with a strong bias. This branch is not used for purposes of practicing the invention. The dotted line represents the continuation of the Lorentz force into the lower magnetic bias region.

The branch 32 represents an increasing dominance of magnetostriction with decreasing magnetic field. The dashed line represents vibrations produced solely by the effect of magnetostriction.

Figure 3B:
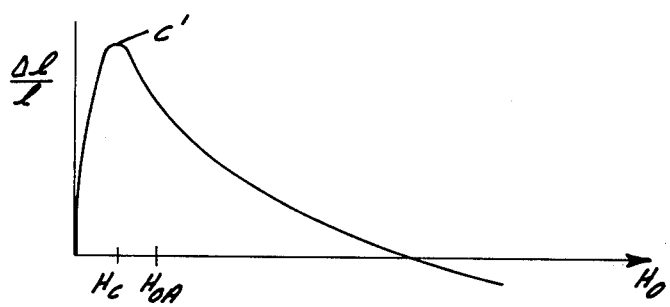
FIG. 3b is a graph plotted in alignment with FIG. 3a for the same abscissa, and showing magnetostrictive length changes as a function of the magnetic bias.

FIG. 3b is plotted in alignment with curve 30 so that corresponding values on the abscissa are vertically aligned. The curve in FIG. 3b represents static relative length changes $\Delta l/l$ in dependence upon an applied magnetic field. One can also say that this curve delineates regions in which the superimposed oscillations in the magnetic field produce zero points in excited mechanical vibrations. Any magnetic field variation will produce a more or less pronounced oscillation in the relative length change $\Delta l/l$ on account of the bias, and that variation is responsible for the generation of vibrations.

The point A of curve 30 denotes a maximum, representing maximum efficiency in the production of surface waves on account of magnetostriction. Thus, if the material is biased to $H_{oA}$, the superimposed magnetic field variation produces largest amplitudes of the generated vibrations. The reason for this is that the relative length change (on account of magnetostriction) as depending on the applied (static) magnetic field, has a large gradient at $H_{oA}$, as can be seen from FIG. 3b, so that a superimposed oscillatory change in magnetic field strength results indeed in a large oscillatory variation in the relative length change, which is merely another way of saying that a large mechanical vibration is being produced.

We discovered that upon decreasing the magnetic bias field from $H_{oA}$, the efficiency of the generation of vibrations exhibits a certain fine structure. Specifically, the amplitude of the surface wave detected drops sharply as per branch 33 to a sharp and well pronounced minimum C. For further decreased magnetic field another, smaller maximum B develops in branch 34 of the curve. The curve merges with the zero-zero point of the plot but only if one neglects (or eliminates) the effect of magnetic hysteresis.

The reason for the existence of this minimum C and for the maximum B can again be derived from the magnetostrictive length change as per FIG. 3b. The relative (static) length change of steel has a maximum (C') at a particular bias $H_c$ being, say, below 200 oersteds. Thus, upon biasing the material magnetically to that point $H_c$, a magnetic field oscillating around that value $H_c$ will vary the relative length change very little. Accordingly, mechanical vibrations are not produced or only to a minor extent. That accounts for the minimum C of curve 30. Upon decreasing the magnetic bias further the relative length change drops from the maximum C' to zero along a fairly steep curve as shown in FIG. 3b. Accordingly, magnetic oscillations around any bias point on that branch result in noticeable vibrations which have a second maximum B of efficiency.

The curve 30 plotted in FIG. 3a, and the magnetostriction curve of FIG. 3b, have been generated for steel. Other ferromagnetic materials have differing characteristics as to efficiency and magnetostriction. However, in practically all instances of magnetostriction, there is a more or less pronounced maximum A of efficiency of generating vibrations on account of magnetostriction. The characteristics of the efficiency at smaller magnetic fields may be even more complex and structured than indicated here.

The reason for this behavior of steel can be summarized as follows. The steel is presumed to be a polycrystal. Magnetostriction along the easy axis of magnetization of a single crystal does not occur until the field is strong enough so that 180° domain wall changes are completed; just reversal of the alignment does not produce any length changes. For higher field strengths domains with a transverse magnetization are rotated by 90°. The resulting relative length change increases with higher field strength and is positive. On the other hand, magnetization along the diagonal axis of crystal requires a larger field strength for completion of domain wall rotations by 180° and 90°, and neither will produce any length change. Still higher field strengths, however, produce domain rotations such that relative length changes do occur and are negative.

A polycrystal, of course, exhibits both kinds of effects so that the resulting magnetostriction is a composite effect. For a stress free sample, this composite curve is of the type shown in FIG. 3b. The curve does have a positive maximum and only for higher field strength does the negative length change prevail. For further details see the paper published by one of us in "Proceedings of the ARPA/AFML, Review of Quantitative NDE Report No. AFML-TR-75-212, page 813 et seq. January 1976."

The curves of FIGS. 3a and 3b have validity only for a stress free, structural material. Though it is generally known (as was mentioned in the background portion above) that magnetostriction is affected by tension and compression, we found more specifically that the fine structure of the efficiency curve ($H<H_{oA}$) varies significantly, while the maximum or peak A remains relatively invariant with stress conditions. Of course, the location $H_{oA}$ on the magnetic bias field abscissa as well as the amplitude of the generated wave does exhibit some variation with the stress condition of the region generating the oscillations, but the fine structure of the characteristics is significantly more affected. Of course, the Lorentz force does not depend on stress conditions.

Figure 4:
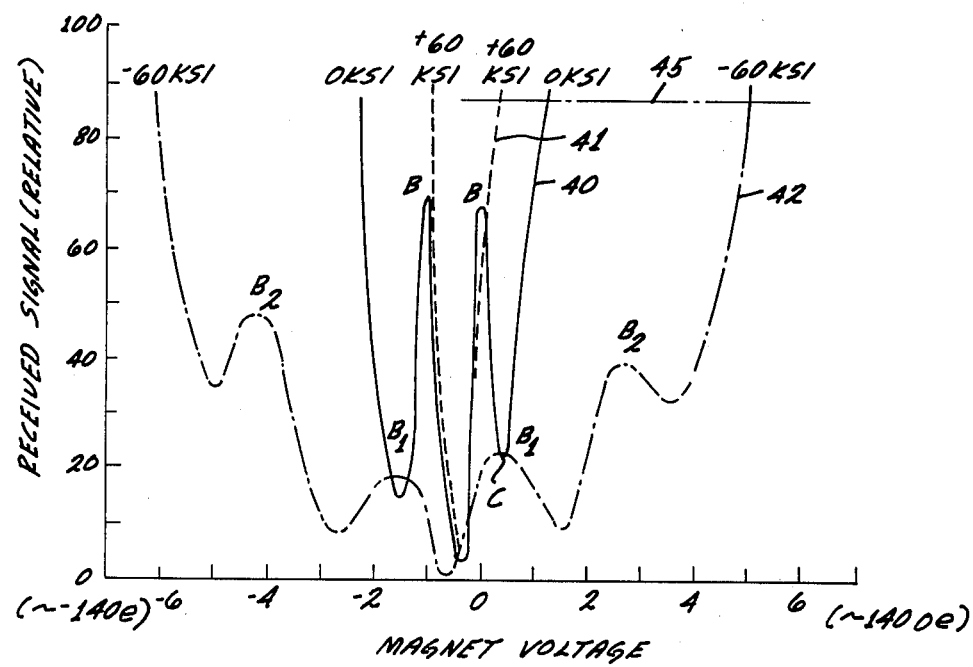
FIG. 4 is a graph showing the efficiency of generation of vibrations vs. magnetic bias in steel for different stress conditions.

FIG. 4 shows the low field portion of an efficiency plot but for different stress conditions. For reasons of demonstration, the abscissa represents driving voltage for the coil 12, because such a driving voltage is directly available as a measuring quantity. Curve 40 represents the stress free state for 1018 steel and, thus, corresponds generally to curve 30 in FIG. 3. However, if tensile stress is applied to, or is present in the part, the maximum B and the minimum C tend to be obliterated. Curve 41 is the efficiency characteristics when +60 KSI tension is applied. The branches 33, 34, as per the stress free curve of FIG. 3A, have merged in one downward slope from peak A. In other words, for a given magnetic bias below level A, the generation of vibrations becomes more efficient generally. For example, a magnetic bias equal to the value for which the stress free material has the minimum C, will now cause a much greater amplitude in any vibration.

The reason for this behavior is the following. The tensile stress has very little influence on the magnetostriction for a field in the direction along the diagonal axis of a crystal (111 axis). It will be recalled that a magnetic field along the diagonal axis will first produce 90° and 180° domain wall changes which are not accompanied by any length change. For stronger magnetic fields, the material decreases in length, but tension has little effect on the domain wall changes in relation to any 111 domain axis. However, tension tends to decrease and obliterate magnetostriction along the easy axis of a crystal, because the energy of parallel or antiparallel domains is decreased with respect to perpendicular domains. Thus, fewer 90° wall motions will occur and magnetostriction becomes less pronounced accordingly. As a consequence, recalling that a polycrystal exhibits both kinds of response, the magnetostriction (relative length change) for highly tensioned material tends to be increasingly negative for increasing field bias with no pronounced maximum. We believe that this behavior is responsible for the obliteration of the minimum C in the efficiency of the production of vibrations. Stress tends to obliterate the fine structure in the characteristics.

Curve 42 in FIG. 4 represents the efficiency of production of elastic vibrations generally, particularly of surface waves, of the material placed under compressive stress of −60 KSI. The curve becomes more complex, and greater efficiency is obtained only for a higher bias value. The explanation for this behavior is to be seen in the fact that magnetic domains under compression stress will tend to be oriented perpendicular to the axis of compression and that, in turn, accounts for a greater number of 90° changes at lower field strengths to obtain alignment along the easy axis of magnetization. The compression does not affect the magnetization along the 111 axis. Thus, positive and negative length changes tend to be more balanced which accounts for an overall smaller length change and greater complexity in the contour of the efficiency of producing vibrations on account of magnetostriction.

It should be mentioned briefly that curves 40, 41, and 42 are not symmetrical on account of hysteresis. The curves were generated by beginning the bias from source 13 with a rather high d.c. current in coil 12 saturating the zone 4 underneath, and by reducing the bias to zero followed by reversal and increase to saturation in the opposite direction. Under these conditions asymmetry will be the more pronounced the greater the hysteresis spread.

The line 45 represents how these different characteristics can be used. Basically, this line 45 represents an (at first) arbitrarily selected amplitude for the surface waves as received. For the same material and the same transducer spacing, the intersections with curves 40, 41, and 42 represent three points corresponding to three different abscissa values for the magnetization bias. Upon adjusting the magnetic field (adjustment of current and voltage from source 13) until instrument 22 indicates the same selected value (efficiency), one obtains a representation of the stress condition in the material. In other words, the different magnetization bias needed to obtain the same efficiency in the generation of vibrations on account of magnetostriction, is a representation of the existing stress condition in the zone of generation of these vibrations.

In the simplest fashion, this method of acquiring stress data can be used on a relative scale. For example, the transducer assembly is placed on different points and areas of an object and for each position the magnetic field defining parameter, voltage and current, are adjusted to obtain the same output level of transducer 20 as indicated at 22.

A more methodical approach, particularly for purposes of obtaining absolute values is the following. The transducer assembly is positioned, for example, on a sample or specimen of the material known to have zero or minimal stress. Next, a strong current is produced to flow through coil 12 to positively saturate the material, so that one is at a point on the characteristics (FIG. 3a)

to the right. Next, the current in coil 12 is reduced for reducing the magnetic biasing field, while the instrument 22 is read. Passage of point A in the characteristics is marked by a particular magnitude in the signal readout flanked by smaller values and representing a pronounced maximum in the reception of surface waves, i.e., efficiency.

Having found the peak A the magnetic bias is now reduced until the amplitude of the detected vibrations and surface waves has a level of about one-third of the peak amplitude value, i.e., the magnetic bias field is reduced until the amplitude of the acoustic waves as received has about one-third of the value corresponding to maximum magnetostrictive efficiency at the existing zero stress condition.

It was found that this one-third level is very suitable for use as stress indicator. In other words, the measuring characteristics 45 as per FIG. 4 should be placed at a level for received signals of one-third the peak amplitude value of A. It was found that, for example, the drive voltage from source 13 to produce a constant acoustic signal level will vary significantly with stress, and can be used to obtain a measure of the stress in a material in which the stress is unknown.

This particular bias or point of origin for measurement can be prepared as described by placing the two transducers in particular positions on a structural part to be used for reference purposes. Upon placing the transducers on a different part of the same material or on a different surface portions of the same part, one can proceed analogously by first searching for the maximum efficiency peak A, and by reducing the bias to, e.g. the one third level of amplitude reading as per instrument 22. The magnetic bias needed to sustain that level of efficiency is an indication of stress relative to the reference reading made earlier. Please note that the measurement readings quite invariant to local surface conditions and transducer spacing if for each new set up of the transducers one searches first for the peak A which is invariant (to a considerable extent) to stress. The actual detected efficiencies and reading with instrument 22 for the peak A in each instance may well differ for different set-ups, surface conditions, etc., but if one reduces the magnetic bias to a fixed fraction of the effective efficiency reading, e.g. to the one third level of the peak A efficiency in each instance, then the local conditions, transducer spacing, etc., cancel out and the magnetic bias values needed for producing the one-third-peak efficiencies become comparable and are directly stress related.

Another method can be carried out as follows. Having chosen a reference efficiency level of one third of peak A efficiencies, the transducer pair can now be placed in different locations and without searching again for the peak efficiency thereat, the needed adjustment in current flow for the d.c. magnetic bias for retaining the efficiency level is a direct indication of stress provided, of course, the transducer spacing remains the same. In order to obtain relative readings, the two transducers may simply be placed on different surface portions and different readouts will yield information on relative stress conditions or stress differentials.

Figure 5:
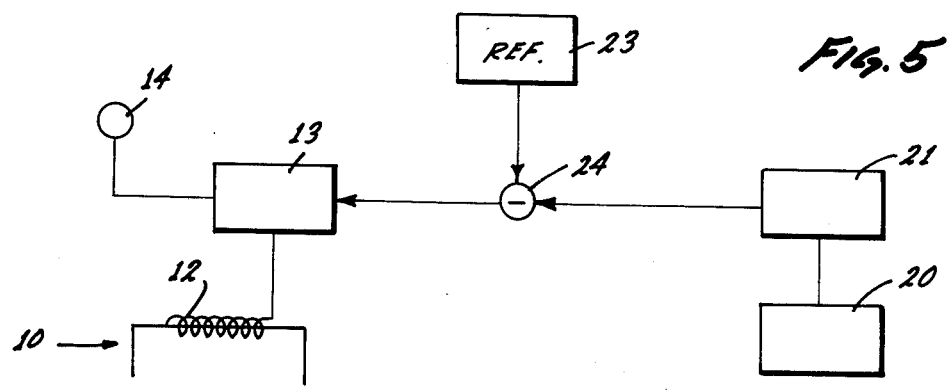
FIG. 5 is a block diagram for illustrating how the equipment shown in FIG. 2 can be operated in a closed loop.

The operation may be automated by connecting source 13 and readout circuit 21 in closed loop configuration. As shown in FIG. 5, the signal furnished by transducer 20 and as amplified in 21 is compared with a reference signal from a source 23. The reference signal represents the desired amplitude value, e.g., one-third down from the maximum signal corresponding to peak A (FIG. 3a). A difference forming or negative summing point 24 establishes an error signal which is used to adjust the source 13. The resulting output voltage or current driving coil 12 is used also here as measured value being indicated by instrument 14.

As the transducers 10, 20 are shifted over the surface, instrument 14 gives a running indication of the stress condition in the region of production of vibrations in any instance. Transducers 10 and 20 may be mounted in a common frame or the like so that their moving across the surface is facilitated. The spacing between the transducers 10 and 20 must remain the same in order to obtain comparable readings.

As was mentioned earlier, the essential aspect of the readout value is its representation of the efficiency of the generation of vibrations, e.g., surface waves. The variations thereof with stress are generally of larger amplitude than variations in the wave propagative properties that may be encountered. Of course, gross surface irregularities may influence the measured result but could be avoided. However, as was mentioned earlier, by seeking the peak efficiency level A anew for each location, and operating consistently at one-third efficiency level as derived from each newly found peak A, one can eliminate surface irregularities.

Another aspect is the following. Upon placing the transducer 10 on a particular spot and turning it on its center while transducer 20 is correspondingly placed in positions on a circle around that center, one obtains a series of readouts which is indicative of the orientation of the stress axis or any other anisotropy which may constitute valuable information in itself.

The stress measurement outlined above uses efficiency of generation and production of vibrations only indirectly in that one searches for the particular magnetic bias which will produce the same efficiency in each instance. In terms of operation, this aspect is represented by placing the measuring characteristics 45 in a selected signal amplitude level. This is very convenient, but not inherently necessary. One could place the characteristic vertically which means that the magnetization is kept constant and the amplitude of the signal as received varies with stress conditions. However, the former method is preferred, because less prone to ambiguity.

It should be noted that the various structural materials have greatly different efficiency curves, but the spread in the sense that different bias magnetizations are required for different stress conditions to obtain the same vibration amplitudes at a level below the always present peak A, is clearly the most reliable indicator. Stress vs. magnetization bias seems to be quite a monotonic function, at least for a large variety of materials exhibiting magnetostriction at least to some degree.

It will be appreciated that the efficiency of generation of vibrations in absolute terms is also related to the size of the region 4 participating in the process. The area covered by transducer 10 in a first experiment was about 1.5 inches squared. Since the depth of the region affected by the internal oscillating magnetic field depends on the frequency of these oscillations on account of the skin effect, the depth of that region participating in the generation of the vibrations depends on the frequency accordingly. For 160 kHz that depth is above 10 mills. For 1 MHz the depth would be about 3 mills. Thus, a change in frequency permits less deep or deeper probing of the stress conditions in the interior of the material. Upon using different frequencies one must use different spacings of the conductors of coil 15. These coils 15 may be placed on individual PC boards as stated and can simply be exchanged so that for each operating frequency the coil with the correct conductor spacing ($\lambda/2$) be used.

The areal dimensions of the transducer 10 could well be smaller so that the stress conditions in the structural part could be determined at a correspondingly higher resolution. Particularly for detail studies, one could use also a mode of operation in which the bias is kept constant, and the oscillating component (source 16) is varied to obtain a constant readout amplitude in the pickup circuit.

The inventive method has been explained on the basis of utilizing surface waves as intermediary for obtaining an indication of efficiency of the generation of vibrations. Other transducers can be used to generate bulk waves and they are also suitable indications.

It should be noted that the particle displacement in the surface of the structure part 1 is a rotational one. Bulk waves may be detected on account of reflection at the back wall of part 1. The pickup transducer may, in that case, be located on an opposite surface, in the line of "sight" for vibrations which travel straight down. If the part of structural material under investigation is relatively thin, one may actually generate Lamb waves. Generally speaking, one will use vibrations that represent best the generation process and are very little influenced by the propagation. Another modification in the method is to be seen in using the transducer 10 as pickup while launching waves with 20. Bias coil 12 is operated as before, but coil 15 detects the amplitude of the magnetic field variations that occur in region 4 on account of the magnetic bias of that region and as affected by incoming elastic vibrations. In this case, one will detect the efficiency of generating the variable field due to the reciprocity of magnetostriction.

The invention is not limited to the embodiments described above but all changes and modifications thereof not constituting departures from the spirit and scope of the invention are intended to be included.

We claim:

1. A method of measuring stress in a part of a structural material comprising the steps of:
   generating magnetically in the material vibrations as a result of alternation of magnetostriction in the material and in a well defined first location of the structural part;
   detecting at a different location the vibrations as generated and launched from the first location, thereby producing a signal having a particular amplitude;
   deriving from the preceding steps a representation of the efficiency of the generation of the vibrations at said first location; and
   comparing the representation with a representation of a generation of vibrations generated and detected in a similar manner but at a different location of the same part or at a location of a different part of the same material.

2. A method as in claim 1 wherein the generating step is a composite step of
   a. magnetically biasing the said location; and
   b. superimposing an oscillatory component upon the bias; the efficiency being given by the relation of the magnetic bias and the amplitude of the detected vibrations.

3. A method as in claim 2 wherein the said representation is the bias needed to obtain said particular amplitude.

4. A method as in claim 2 wherein the representation is the amplitude for a given bias.

5. A method as in claim 2, wherein the said representation is an amplitude of the oscillatory component for a given bias and a particular amplitude of detected vibrations.

6. A method of measuring stress in a part of a structural material, comprising the steps of:
   generating vibrations in the part which step includes
   a. magnetically biasing a region of said part; and
   b. superimposing oscillatory magnetic field upon the bias;
   detecting vibrations as transmitted from said region; and providing a signal representing the detected amplitude, the signal in correlation with the biasing representing the stress condition in the region of said part.

7. The method as in claim 6, wherein the biasing step includes biasing the region by a magnetic field weaker than needed for generating vibrations magnetostrictically of maximum amplitude.

8. Method of detecting microstructure conditions in a part of a structural material such as stress, plastic deformation, dislocations, etc., comprising the steps of generating in a region of said part magnetostrictive oscillations, and detecting efficiency of the generation in representation of the microstructure conditions in said region.

9. The method as in claim 8, wherein the detecting step includes the detection of surface waves in the part.

10. The method as in claim 8, wherein the detecting step includes the detection of bulk waves in the part.

11. The method as in claim 8, wherein the detecting step includes the detection of Lamb waves in the part.

12. The method as in claim 8, wherein the generating step includes the electromagnetic generation of magnetostrictive vibrations in the part.

13. The method as in claim 8, wherein the generating step includes the magnetostrictive generation of a variable magnetic field on the basis of elastic vibrations.

14. A method of detecting microstructure conditions in a structural material, such as stress, plastic deformation, dislocations, comprising:
   magnetically biasing a particular region of the material;
   causing magnetostrictive oscillations to be generated in the particular region of the material; and
   detecting the efficiency of the generation in representation of the microstructure conditions of the said region.

15. Method as in claim 14, said oscillations being elastic vibrations generated by applying oscillations of a magnetic field to said region and superimposing them upon said bias, the detecting step including detecting an amplitude of the elastic vibrations as generated.

16. Method as in claim 14, said oscillations being oscillations of magnetizations resulting from elastic vibrations in said region, the detecting step including detecting an amplitude of the oscillations of magnetization.

17. Method as in claim 14, wherein first signals are used for generating said oscillations and second signals are produced pursuant to the detecting, the detection of the efficiency including maintaining said magnetically biasing constant and said first signals constant and detecting the amplitude of the third one.

18. A method of measuring stress in a part of a structural material, comprising the steps of:
magnetically biasing a first region of said part; magnetically exciting the first region to obtain magnetostrictive oscillations;
detecting mechanical vibrations as emitted by said first region;
repeating the aforementioned steps for a different region of the same part of a different part;
determining the magnetic bias and the detected vibrations as per said aforementioned steps as well as repeated; and
deriving a representation of the relative stress in the first and second regions from said determined biases and from said detected vibrations.

19. A method as in claim 18, and including the steps of adjusting the biasing to obtain constant amplitudes, the adjusted bias for the first and second regions representing the relative stress therein.

20. A method as in claim 18, and including the steps of determining said amplitudes for constant bias.

21. A method of measuring stress in a part of a structural material, comprising the steps of:
generating a magnetic field in a limited region in said part;
causing said field to vary at a particular high frequency so that vibrations are generated in the region on account of magnetostriction;
detecting the vibrations at a location spaced-apart from said region, said vibrations as detected having a maximum value for a first particular value of the magnetic field, the magnetic field as generated pursuant to the generating step being smaller than the first particular value;
deriving from the preceding steps an indication of the efficiency of the generation; repeating the previous steps for a different location; and
comparing the resulting indications with each other to obtain a repesentation of the relative stress conditions in said locations. representation 22. The method as in claim 21, wherein the generating step includes:
a. providing of a magnetic bias; and
b. superimposing a variable magnetic field.

23. The method as in claim 22, wherein said bias is adjustable and the representations are adjusted values for said bias, to obtain detected vibrations of constant amplitude.

24. The method as in claim 22, wherein the indications are amplitude values of the variable magnetic field at each of said different locations, and including the step of holding the bias and detected vibrations to constant values.

25. The method as in claim 21, including the step of holding the bias constant, the representations being amplitude values as detected for the constant bias.

26. A method of measuring stress in a structural material, comprising the steps of:
i. generating a first signal being a magnetic biasing field to be effective in limited region of the material;
ii. superimposing a second signal being an oscillatory component, upon said biasing field so that vibrations are generated in the region on account of magnetostriction;
iii. detecting said vibrations at locations spaced from said region and generating a third signal representative thereof;
maintaining two of said first, second and third signals constant; and
deriving an indication of the efficiency of the generation of said vibrations from the resulting value of the remaining signal, said indication being representative of the stress in said region.

27. A method of detecting stress in structural material comprising:
magnetically biasing a particular region;
generating an oscillating magnetic field in said region;
detecting elastic vibrations as produced in said region including detecting a maximum in the amplitude of the vibrations by varying said biasing;
reducing said biasing so that the vibrations as detected have an amplitude which is a particular fraction of the said maximum; and
determining a quantity representative of the bias as reduced.

28. A method of measuring stress in a part of a structural material comprising the steps of:
generating magnetically in the material vibrations as a result of alternation of magnetostriction in the material and in a well defined first location of the structural part by (a) magnetically biasing said location, and (b) superimposing an oscillatory component upon the bias;
detecting at a different location the vibrations as generated and launched from the first location, thereby producing a signal having a particular amplitude;
deriving from the preceding steps a representation of the efficiency of the generation of the vibrations at said first location by determining the magnetic bias needed to obtain said particular amplitude; and
comparing the representation with a representation of a generation of vibrations generated and detected in a similar manner but at a different location of the same part or at a location of a different part of the same material.

29. A method of measuring stress in a part of a structural material, comprising steps of:
magnetically biasing a first region of said part;
magnetically exciting the first region to obtain magnetostrictive oscillations;
detecting mechanical vibrations as emitted by said first region;
adjusting the biasing to obtain constant amplitudes of said vibrations;
repeating the aforementioned steps for a different region of the same part or a different part;
determining the magnetic bias and the detected vibrations as per said aforementioned steps as well as repeated; and
deriving a representation of the relative stress in the first and second regions from said adjusted biases for the first and second regions.

30. A method of measuring stress in a part of a structural material, comprising the steps of:
generating a magnetic field in a limited region in said part by providing an adjustable magnetic bias and superimposing a variable magnetic field;
causing said field to vary at a particular high frequency so that vibrations are generated in the region on account of magnetostriction;
detecting the vibrations at a location spaced-apart from said region, said vibrations as detected having a maximum value for a first particular value of the magnetic field, the magnetic field as generated pursuant to the generating step being smaller than the first particular value;

deriving from the preceding steps an indication of the efficiency of the generation by adjusting said bias to obtain detected vibrations of constant amplitude;

repeating the previous steps for a different location; and comparing the resulting indications with each other to obtain a representation of the relative stress conditions in said locations.

* * * * *